United States Patent
Solaun et al.

(10) Patent No.: US 12,369,920 B2
(45) Date of Patent: Jul. 29, 2025

(54) INTRODUCER SHEATH HAVING AN INTENTIONAL FRICTION ZONE TO HOLD IN POSITION A DELIVERY SYSTEM SUITABLE FOR IMPLANTABLE INTRAVASCULAR DEVICES

(71) Applicant: DePuy Synthes Products, Inc., Raynham, MA (US)

(72) Inventors: Daniel Solaun, Miami, FL (US); David Blumenstyk, Miami, FL (US); Chelsea Dahline, Coral Gables, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 203 days.

(21) Appl. No.: 17/482,373

(22) Filed: Sep. 22, 2021

(65) Prior Publication Data
US 2023/0089430 A1    Mar. 23, 2023

(51) Int. Cl.
*A61B 17/12*    (2006.01)
*A61B 17/00*    (2006.01)

(52) U.S. Cl.
CPC .... *A61B 17/1214* (2013.01); *A61B 17/12113* (2013.01); *A61B 2017/00526* (2013.01); *A61B 2017/1205* (2013.01)

(58) Field of Classification Search
CPC .......... A61B 17/1214; A61B 17/12113; A61B 2017/00526; A61B 2017/1205; A61M 2025/0681; A61M 25/0009; A61M 25/0662; A61M 25/0045; A61M 25/0043
See application file for complete search history.

(56) References Cited

U.S. PATENT DOCUMENTS

| 3,149,186 | A | 9/1964 | Coanda |
| 6,408,214 | B1 * | 6/2002 | Williams .......... A61M 25/0041 607/122 |
| 7,090,681 | B2 | 8/2006 | Weber et al. |

(Continued)

FOREIGN PATENT DOCUMENTS

| CN | 112 604 126 | 4/2021 |
| CZ | 21698 U1 | 11/2010 |

(Continued)

OTHER PUBLICATIONS

EP Search Report of counterpart Application Serial No. EP 22196746. 6-1122, dated Feb. 27, 2023 (11 pp.).

*Primary Examiner* — Vi X Nguyen
(74) *Attorney, Agent, or Firm* — TROUTMAN PEPPER LOCKE LLP

(57) ABSTRACT

An intravascular treatment system including an introducer sheath having an intentional friction zone along a section thereof imposing an intentional friction force on the outer surface of a catheter shaft slidable therein. The friction zone representing a non-straight (e.g., curved or bent) section of the introducer sheath and/or a section of the introducer sheath whose inner wall has a reduced inner diameter (e.g., fused heat shrink material). During intravascular treatment, sufficient axial force may be applied to overcome the imposed intentional friction force and advance the intravascular treatment device in a distal direction to a desired target site in the artery. Once properly positioned, the imposed intentional friction force ensures that the intravascular treatment device is maintained in place.

19 Claims, 9 Drawing Sheets

(56) References Cited

U.S. PATENT DOCUMENTS

| | | | |
|---|---|---|---|
| 7,699,862 B2 | 4/2010 | Gorospe | |
| 7,819,889 B2 | 10/2010 | Healy et al. | |
| 8,133,252 B2 | 3/2012 | Davis et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,943,313 B2 | 4/2018 | Jones et al. | |
| 2004/0104512 A1 | 6/2004 | Eidenschink | |
| 2005/0165366 A1* | 7/2005 | Brustad | A61M 25/0043 604/264 |
| 2009/0143808 A1 | 6/2009 | Houser | |
| 2014/0194822 A1* | 7/2014 | Wu | A61M 25/0662 604/171 |
| 2015/0272735 A1 | 10/2015 | Kaufmann | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2020/0288952 A1* | 9/2020 | Jurevicius | A61B 8/12 |
| 2021/0205577 A1* | 7/2021 | Jalgaonkar | A61M 25/0052 |

FOREIGN PATENT DOCUMENTS

| | | |
|---|---|---|
| IE | 20100752 A2 | 8/2011 |
| WO | 2018022186 | 2/2018 |

* cited by examiner

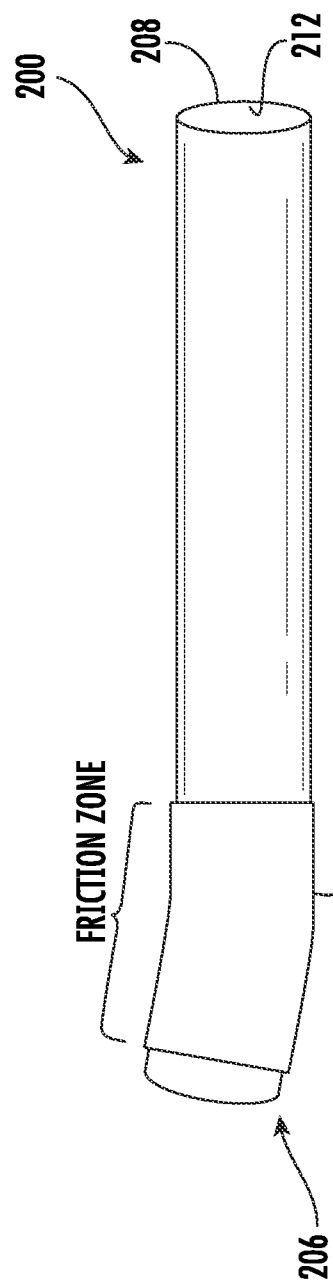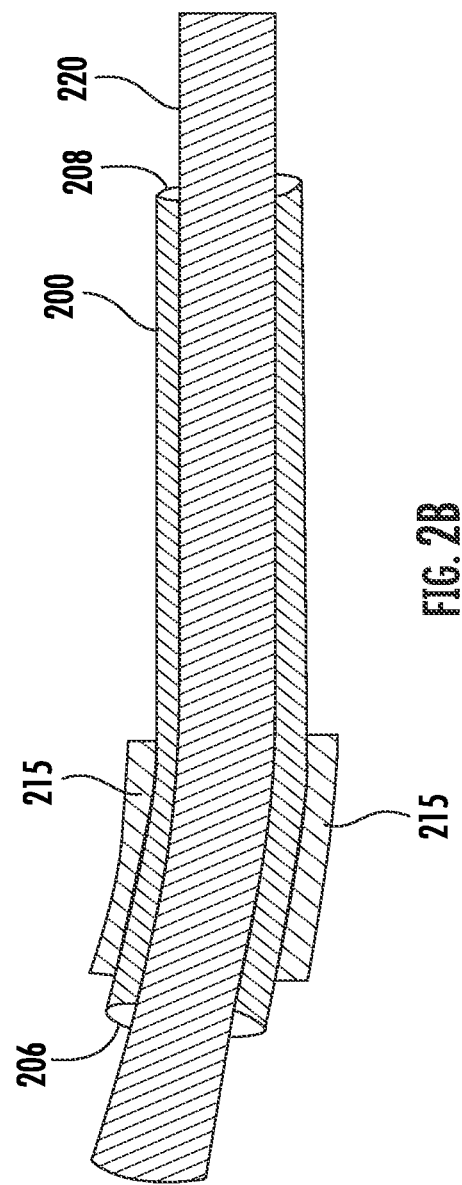

INTRODUCER SHEATH HAVING AN INTENTIONAL FRICTION ZONE TO HOLD IN POSITION A DELIVERY SYSTEM SUITABLE FOR IMPLANTABLE INTRAVASCULAR DEVICES

FIELD OF THE INVENTION

The present invention relates to an intervascular intervention system for delivery of an implantable intravascular device used during an endovascular treatment or procedure. In particular, the present invention is directed to an introducer sheath having an intentional friction zone to maintain in position a delivery system suitable for use with implantable intravascular devices (e.g., embolic coils) of varying outer diameter during endovascular treatment (e.g., brain aneurysm).

DESCRIPTION OF RELATED ART

Implantable intravascular devices are commonly used in the endovascular procedures or treatments of various vascular ailments, for example, brain aneurysms. A catheter is inserted into the femoral artery in patient's leg and guided by imaging navigated through the vessel to the target site in the brain where the aneurysm is located. With the distal end of the catheter properly positioned on a proximal side of the aneurysm, a microcatheter is tracked through the catheter to the proximal side of the aneurysm. A delivery and deployment system loaded with an implantable intravascular device (e.g., embolic coil) is introduced via the microcatheter to the target site. During delivery to the target site, the implantable intravascular device is secured to the delivery system, typically via a wire. When properly positioned at the target site (e.g., at the location of the aneurysm) the wire is severed or detached releasing the implantable intravascular device (e.g., embolic coil) to be deposited within the aneurysm. This process is repeated until the area of the vessel with the weakened wall is tightly packed with numerous embolic coils occluding blood flow thereto thereby preventing rupture. Severing of the embolic coil from the securement wire is typically achieved by passing of a small electrical current through the wire.

During delivery of an implantable intravascular device to a target site within the artery or vessel, conventional intravascular intervention systems have heretofore employed various engageable mechanical configurations associated with a conventional straight introducer sheath. U.S. Pat. No. 7,699,862 is directed to a reloadable slotted introducer sheath and vaso-occlusive device that when passed through a distal portion of a resheathing tool, the resheathing tool serves to lock in place the reloadable slotted introducer sheath and vaso-occlusive device together. Related patents (U.S. Pat. Nos. 8,133,252 & 7,819,889) describe an introducer sheath having a side opening defined in the outer wall radially inward to the lumen with a longitudinal slit extending from the side opening toward a distal end. These devices require complex alignment and engagement of components to operate properly.

It is desirable to develop an improved simplified introducer sheath able to maintain the position of the delivery system without the need for alignment of complex mechanical engageable components that is also universally suitable for use with coils of varying outer diameter.

SUMMARY OF THE INVENTION

The present invention is directed to an intravascular intervention system including an introducer sheath having at least one intentional friction zone along a section thereof imposing an intentional friction force on the outer surface of a catheter shaft slidable therein. The friction zone representing a non-straight (e.g., curved or bent) section of the introducer sheath and/or a section of the introducer sheath whose inner wall has a reduced inner diameter (e.g., fused heat shrink material). During intravascular treatment, sufficient axial force may be applied to overcome the imposed intentional friction force and advance the intravascular treatment device in a distal direction to a desired target site in the artery. Once properly positioned, the imposed intentional friction force ensures that the intravascular treatment device is maintained at the desired target site when being deployed.

Another aspect of the present invention relates to a method of manufacturing an introducer sheath of an intravascular intervention system. A straight introducer sheath having a proximal end, an opposite distal end, and a longitudinal lumen of uniform inner diameter defined therebetween is provided. Radially about an outer surface of the introducer sheath a heat shrink material is positioned. Into the longitudinal lumen of the straight introducer sheath a non-straight mandrel is inserted. Then, heat is applied at a predetermined temperature for a predetermined period of time sufficient to cause a section of the introducer sheath to be molded to include an intentional friction zone conforming to the non-straight mandrel and the heat shrink sleeve to reflow about the molded intentional friction zone forming an assembled structure. Thereafter, the non-straight mandrel is removed from the formed assembled structure including the molded introducer sheath having the intentional friction zone together with the reflow heat shrink sleeve.

Another aspect of the present invention is directed to a method of manufacturing an introducer sheath of an intravascular intervention system by providing a straight introducer sheath having a proximal end, an opposite distal end, and a longitudinal lumen having a uniform inner diameter therebetween A heat shrink material is applied to a section of an inner wall of the straight introducer sheath and thereafter a straight mandrel is inserted into the lumen of the straight introducer sheath. Heat is applied at a predetermined temperature for a predetermined period of time sufficient to reflow the applied heat shrink material reducing the inner diameter of the longitudinal lumen along the section of the inner wall of the straight introducer sheath forming an intentional friction zone of an assembled structure. Finally, the straight mandrel is removed from the assembled structure.

Still yet another aspect of the present invention relates to a method for using an intravascular intervention system by providing an introducer sheath having a proximal end, an opposite distal end, a longitudinal lumen with an inner diameter extending therebetween the proximal and distal ends, and an intentional friction zone along a section of the introducer sheath. Next, a catheter shaft is introduced into the longitudinal lumen of the introducer sheath. During advancement to a target position, sufficient force is applied in a distal direction on a proximal end of the catheter shaft to overcome an intentional frictional force imposed by the intentional friction zone of the introducer sheath on an outer surface of the catheter shaft. Upon reaching the target position, the catheter shaft is retained at the target position by the imposed intentional frictional force.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 2A is a side view of an exemplary embodiment of the present inventive introducer sheath having a non-straight (non-parallel to the longitudinal axis therethrough) (e.g., curved or bent section) intentional friction zone disposed along a proximal section of the introducer sheath with a heat shrink sleeve;

FIG. 2B is a longitudinal cross-sectional view of the present inventive introducer sheath of FIG. 2A by which the intentional friction zone is formed by insertion in the lumen thereof of a non-straight (curved) mandrel;

DETAILED DESCRIPTION OF THE INVENTION

Figure 1:
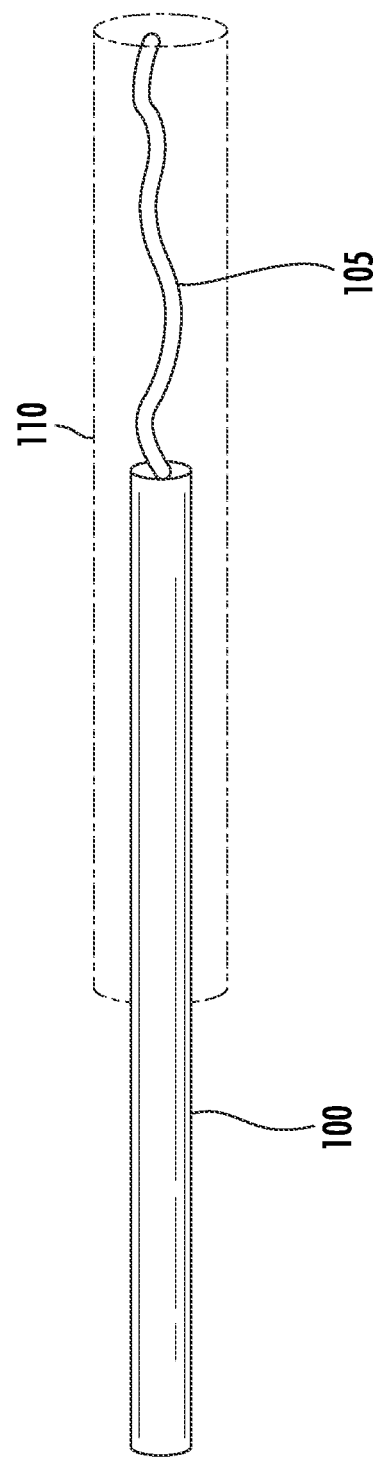
FIG. 1 is a Prior Art assembly comprising a conventional intravascular intervention system including a straight introducer sheath (parallel to the longitudinal axis cylindrical tubing) together with a delivery system having an implantable intravascular device (e.g., embolic coil) loaded therein.

In the description, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

During an endovascular treatment procedure (e.g., coil embolization), it is desirable for the delivery and detachment/deployment system to reliably deliver and deposit the implantable intravascular device (e.g., embolic coil) at a precise location or target site (e.g., aneurysm) within a vessel or artery. The implantable intravascular device (e.g., embolic coil) is secured to the distal end of a delivery system that together as a unit are advanced to a target site in the vessel or artery via a conventional introducer sheath representing a straight (parallel to the longitudinal axis running therethrough) tubing, as illustrated in the exemplary prior art assembly of FIG. 1. Delivery system 100 has an outer diameter of approximately 0.014". Secured to the distal end of the delivery system 100 is a coil 105 (implantable intravascular device) with an outer diameter of approximately 0.009". Together the delivery system loaded with the coil as a unit are receivable so as to freely slide in an axial direction within the lumen of the conventional straight introducer sheath 110 having an inner diameter of approximately 0.017". The conventional introducer sheath representing a straight (parallel to the longitudinal axis configuration) cylindrical tubing minimizes any direct physical contact or engagement (thus minimizing any non-intentional or undesirable friction force) between the inner wall of the lumen of the conventional straight introducer sheath and the outer surface of the delivery system slidable in a longitudinal direction therein. Any unintentional, de minimis, or negligible friction resulting from undesirable/unintentional direct physical contact between the outer surface of the delivery system and the inner wall of the lumen of the conventional introducer sheath is to be avoided or minimized as much as possible to provide as smooth a delivery of the system as possible.

Different delivery systems each having different size outer diameters are used by interventionalists to deliver embolic coils of varying outer diameter. For instance, coils having an outer diameter range of approximately 0.009" to approximately 0.016" are delivered using a delivery system that itself has an outer diameter of less than approximately 0.015". It would be advantageous to construct a universal introducer sheath suitable for use with a conventional delivery system for delivering conventional implantable intravascular devices (e.g., embolic coils) of varying size outer diameters. Opposing factors are taken into consideration when designing a universal introducer sheath. On the one hand, the inner diameter of the introducer sheath is desirably as large as possible so as to accommodate (receive and allow to freely slide in an axial direction therein) delivery systems suitable for delivery of diverse outer diameters. However, on the other hand, if the inner diameter of the lumen of the introducer sheath is made too large those delivery systems having a significantly smaller outer diameter relative thereto may undesirably shift in position when located at the target site resulting in imprecise deposit or placement of the coil in the artery. Moreover, during retrograde flushing (e.g., using saline) if not securely retained in place the delivery system may undesirably be pushed out from the proximal end of the introducer sheath. The present inventive universal introducer sheath solves the aforementioned concerns by having a sufficiently large inner diameter ranging, for example, from approximately 0.012" to approximately 0.023" for use with a delivery system able to accommodate implantable intravascular devices of different size outer diameters, yet nevertheless maintain the position of the delivery system and implantable intravascular device loaded therein (i.e., minimizing or preventing altogether shifting or falling out) by intentionally introducing a friction zone along one or more discrete sections of the introducer sheath. The intentional friction zone provided in the present inventive introducer sheath is an inexpensive and simplistic design that maintains the position of the delivery system therein while eliminating the need for proper alignment of conventional mechanical engaging mechanisms. This user-friendly simplification of the present inventive introducer sheath eliminates the dexterous physical manipulation of mechanical components requiring physical alignment in order to engage one another thus eliminating potential malfunction (e.g., unintentional failure of engagement or unintended/premature disengagement). Accordingly, the present inventive introducer sheath having one or more intentionally created friction zone(s) the imparted friction from which is overcome during advancement of the delivery system through the lumen of the introducer sheath (including passing of the distal end delivery system through and beyond the friction zone), while intentionally imparting a desired or controlled amount of frictional force on the outer surface of the delivery system to maintain or hold it in place ensuring that the implantable intravascular device loaded therein is precisely deposited at the target site (e.g., brain aneurysm) in the artery.

The present inventive introducer sheath with at least one intentional friction zone is intended for use with a delivery system having a wide range of outer diameters (for example, in a range of approximately 0.0136" to approximately 0.0156") suitable for use with various implantable intravascular devices having different size outer diameters (for example, ranging from approximately 0.009" to approximately 0.016").

Conventional introducer sheaths (as depicted in FIG. 1) represent cylindrical tubing having a straight (parallel to the longitudinal axis extending therethrough) configuration to minimize or avoid altogether any undesirable friction or direct physical contact/engagement between the outer surface of the delivery system and the inner wall of the lumen of the introducer sheath extending in an axial/longitudinal direction therethrough. In contradistinction to such conventional device, the present invention deliberately and intentionally introduces a friction zone along a desired section (e.g., along a proximal and/or distal section) of the introducer sheath to intentionally impose a targeted or controlled friction force on the outer surface of the delivery system as it is slid through therethrough. Intentional introduction of the friction zone along the present inventive introducer sheath may be achieved in a number of ways, of which each design may be used independently of or simultaneously with one another.

For the purpose of this invention, the term "proximal section" is herein defined to include any axial section or portion of the introducer sheath between a midway point (i.e., midway between an open proximal end and an opposite open distal end) and the proximal end/tip of the introducer sheath. In a preferred embodiment, the proximal section may, but doesn't necessarily, include the midway point and/or the proximal end/tip of the introducer sheath. Similarly, the term "distal section" is hereinafter defined to include any axial section or portion of the introducer sheath between a midway point (i.e., midway between an open proximal end and an opposite open distal end) and the distal end/tip of the introducer sheath. In a preferred embodiment, the distal section may, but doesn't necessarily, include the midway point and/or the distal end/tip of the introducer sheath. As previously noted, the intentional friction zone may be disposed anywhere (e.g., proximal section, distal section and/or anywhere between the proximal and distal ends) along the introducer sheath and may include more than one friction zone.

One exemplary way to create an intentional friction zone in the present inventive introducer sheath is to deliberately alter (e.g., curving or bending) the shape of straight cylindrical tubing so that a friction zone section thereof is no longer straight (i.e., non-straight). The term "non-straight" when describing the present inventive introducer sheath is referring to the friction zone thereof. Outside of the non-straight friction zone, the remaining unaltered sections of the introducer sheath remains straight. The controlled alteration (e.g., curving or bending) of the shape of the altered non-straight intentional friction zone of the introducer sheath increases the direct contact surface area between the inner wall along the friction zone of the introducer sheath and the outer surface of the delivery system thereby intentionally imparting a desired amount of friction between the two components.

The term "curvature/curve/curved/curving" or "bend/bent/bending" when describing the intentional friction zone created along the altered non-straight introducer sheath is expressly defined for the purposes herein to be a non-zero angle relative to a longitudinal axis therethrough. In other words, the non-straight (curved or bent) portion comprising the intentional friction zone is non-parallel to the longitudinal axis through the introducer sheath. Selection of a desired curvature imposes or induces a controlled or targeted friction force on the outer surface of the delivery system during advancement through the lumen of the introducer sheath.

When selecting the controlled or targeted curvature or bend in the introducer sheath two competing broad interests are satisfied. On the one hand, the targeted or controlled imposed intentional frictional force is able to be overcome upon application of a sufficient axial pushing force on a proximal end of the delivery system in a distal direction during advancement of the implantable intravascular device to a target site in the artery. While, on the other hand, the targeted or controlled frictional force induced or imparted is sufficient to ensure that the delivery system is held in place (i.e., prevent or minimize shifting, movement, or translation) within the introducer sheath once the implantable intravascular device is precisely positioned at the target site in the artery. A preferred range of targeted or controlled intentional friction force imposed by the non-straight (curved or bent) intentional friction zone of the introducer sheath on the outer surface of the delivery system is preferably in a range between approximately 2.5 gf to approximately 11 gf. Any range of intentional friction force may be imposed, induced or established, as desired, taking these competing factors into consideration.

The outer surface of the delivery system intentionally directly physically contacts or directly engages with the inner wall of the introducer sheath within the non-straight intentional friction zone (curved or bent section) thereby imparting a controlled or targeted frictional force that maintains the delivery system in place relative to the introducer sheath once the implantable intravascular device has been precisely located at the target site in the artery. FIG. 2A is a side view of an exemplary reshaped introducer sheath 200 with a non-straight (curved or bent) intentional friction zone about which is disposed a heat shrinkable sleeve 215.

The introducer sheath 200 of FIG. 2A is achieved by starting with a cylindrical tubing of a biocompatible material (e.g., Polypropylene (PP) or Polyethylene (PE)) having a straight (parallel to the longitudinal axis) cylindrical tubing structure with an open proximal end 206, an opposite open distal end 208, and a lumen 212 defined axially therethrough. A sleeve 215 made of a biocompatible (medical grade) heat shrinkable material, for example, Polytetrafluoroethylene (PTFE), Fluorinated ethylene propylene (FEP), or Polyether Ether-Ketone (PEEK) is positioned at a desired section (e.g., proximal section) about the outer surface of the straight cylindrical tubing. The axial length of the heat shrink sleeve 215 in the exemplary embodiment is approximately 2 cm. Any desired axial length of the heat shrink sleeve may be selected including spanning the entire length of the introducer sheath.

Referring to the longitudinal cross-sectional view of FIG. 2B, a mandrel 220 having a desired shape curvature or bend is inserted into the straight cylindrical tubing so that the curvature of the mandrel is aligned with the heat shrink sleeve 215 disposed at a desired location about the outer surface of the cylindrical tubing. In the exemplary embodiment of FIG. 2B, mandrel 220 has an outer diameter in the range of approximately 0.01604" to approximately 0.01704" and a curvature/chord diameter of approximately 50.5 mm. These specified values are merely illustrative—the outer diameter of the mandrel and curvature/chord diameter of the curve may be modified, as desired.

Exposure to heat causes the introducer sheath 200 to mold/form/bend to match the curvature of the mandrel. Simultaneously, heat shrink sleeve 215 shrinks/conforms about the outer surface of the introducer sheath 200 with a curvature also matching that of the mandrel. When the heat is removed and the curved mandrel is withdrawn from the molded/shaped introducer sheath 200 heat shrink sleeve 215 cools and hardens about the introducer sheath thus maintaining the curvature or bend matching that of the curved mandrel.

Specifically, heating is applied at a specified temperature for a predetermined duration of time sufficient to soften, reshape, and mold the straight cylindrical tubing to conform with the curvature or bend of the mandrel 220. Simultaneously the heat causes the heat shrinkable sleeve 215 to reflow/shrink/conform about the outer surface of the reshaped or molded (e.g., curved or bent) introducer sheath 200 matching the curve of the mandrel. In the exemplary embodiment of FIG. 2B, curved mandrel 220 was heated in a temperature range of approximately 320° F. to approximately 330° F. for a preferred duration of approximately 30 sec. to approximately 35 sec. The temperature and duration to which the curved mandrel 220 is heated may be selected, as desired, based on one or more factors including: (i) the material of the cylindrical tubing of the introducer sheath 200; (ii) the material of the heat shrink sleeve 215; (iii) the distance between the heating element relative to the part being heated; and (iv) the desired severity of the curve. When heated, pressure from the heat shrink sleeve may, but need not necessarily, result in minimal/negligible collapse (reduction) of the inner diameter of the lumen of the introducer sheath along the friction zone. Any such reduction or change in inner diameter is so negligible or de minimis as to be inconsequential and hence, despite such possibility, hereinafter the inner diameter for this configuration is described as having a substantially uniform (substantially unchanging) inner diameter. Following turning off the heat and withdrawing of the curved mandrel 220, the cooled heat shrink sleeve 215 hardens thereby maintaining the curvature along the friction zone of the introducer sheath 200. As a result of the heat shrink sleeve 215, despite repeated runs or turns of the delivery system therethrough, the introducer sheath 200 nevertheless maintains its curvature or bend and hence intentional friction force imposed on the delivery system when advanced therethrough. Having created along the introducer sheath the friction zone in which at least a portion thereof is non-straight (non-parallel to the longitudinal axis extending therethrough) (e.g., curved or bent) a friction force is imposed between the inner wall of the introducer sheath and the outer surface of the delivery system in direct physical contact or direct engagement therewith maintaining the position of the delivery system therein.

The proximal section along the introducer sheath in the exemplary embodiment of FIGS. 2A & 2B is selected as the intentional friction zone (i.e., section in which the heat shrink sleeve together with the introducer sleeve is curved or bent) so that at no time during implantation in the body does the implantable intravascular device (e.g., embolic coil) loaded in the delivery system directly physically contact or directly engage the introducer sheath (i.e., no contact between the implantable intravascular device and the inner wall of the introducer sheath within the friction zone or elsewhere). It is only the outer surface of the delivery system that directly physically contacts or directly engages only within the friction zone (controlled curvature or bend) of the inner wall of the introducer sheath. In the exemplary embodiment of FIG. 2A, the heat shrink sleeve 215 is disposed so that its proximal edge is in a range of approximately 29 mm to approximately 31 mm from the proximal end 206 of the introducer sheath 200. As previously mentioned, the heat shrink sleeve may span the entire length of the introducer sheath or any desired portion thereof.

It is noted that the mere physical curving or bending of an otherwise straight (linear) cylindrical tubing of the conventional introducer sheath without the use of the heat shrink sleeve in accordance with the present invention is less satisfactory for the intended purpose of creating the present inventive controlled or targeted friction zone. With each run (i.e., repeated sliding of the delivery system in an axial direction within the lumen of the introducer sheath) the degree of friction therebetween lessens as a result of lessening of the curvature. Whereas, the heat shrinkable sleeve disposed along the friction zone in accordance with the present invention (FIG. 2A) ensures that the shape, configuration, and degree of the curvature or bend in the introducer sheath is maintained in concert with the intentional frictional force imparted between the inner wall of the introducer sheath and the outer surface of the delivery system slidable in an axial direction therethrough. Instead of using a heat shrink material the sleeve disposed about the outer surface of and aligned with the curve or bend in the proximal section of the introducer sheath may be made of a biocompatible metal (e.g., titanium) to prevent otherwise undesirable lessening of the curvature (reduction of the introduced friction) occurring with repeated use or runs.

Moreover, the present inventive introducer sheath is illustrated and described, by way of example, as having a single (one) friction zone (i.e., a single discrete curvature or bent section) in the proximal section of the introducer sheath; however, the introducer sheath may have more than one friction zone (each discrete friction zone comprising a curvature or bend) separated a predetermined distance in an axial direction from one another. Moreover, the one or more friction zone(s) may be located along a proximal section, a distal section, or anywhere between the proximal and distal ends of the introducer sheath. The curvature or bend of each discrete friction zone section may, but need not necessarily be, the same in dimensions.

Accordingly, the curvature or bend disposed along one or more sections of the introducer sheath creates an intentional friction zone in direct physical contact/engagement with the outer surface of the delivery system. During advancement to the target site in the vessel, when loaded in the delivery system, preferably the embolic coil (implantable intravascular device) never directly physically contacts or directly physically engages with the friction zone or any other region of the inner wall of the introducer sheath.

Figure 3A:
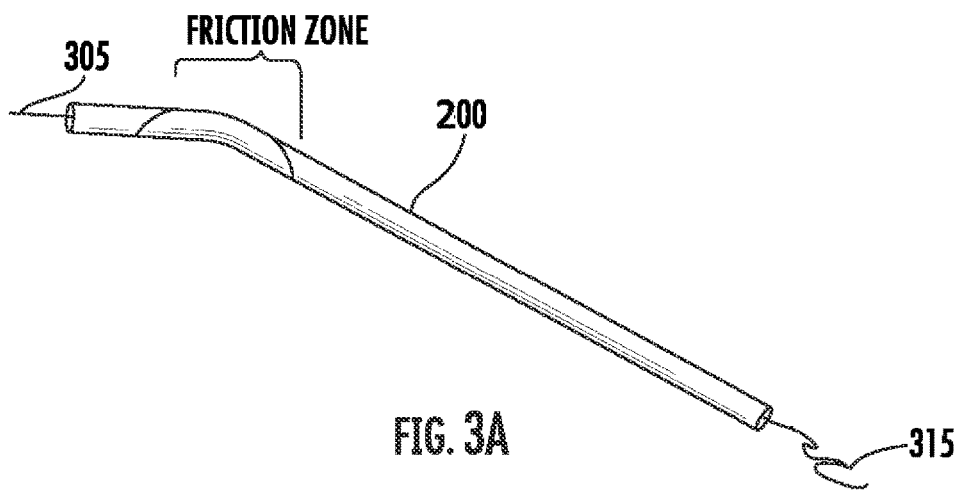
FIG. 3A is a side view of the exemplary assembly of the present inventive intravascular intervention system including the non-straight (curved or bent) intentional friction zone introducer sheath of FIG. 2A together with the delivery system having an implantable intravascular device loaded therein.
Figure 3B:
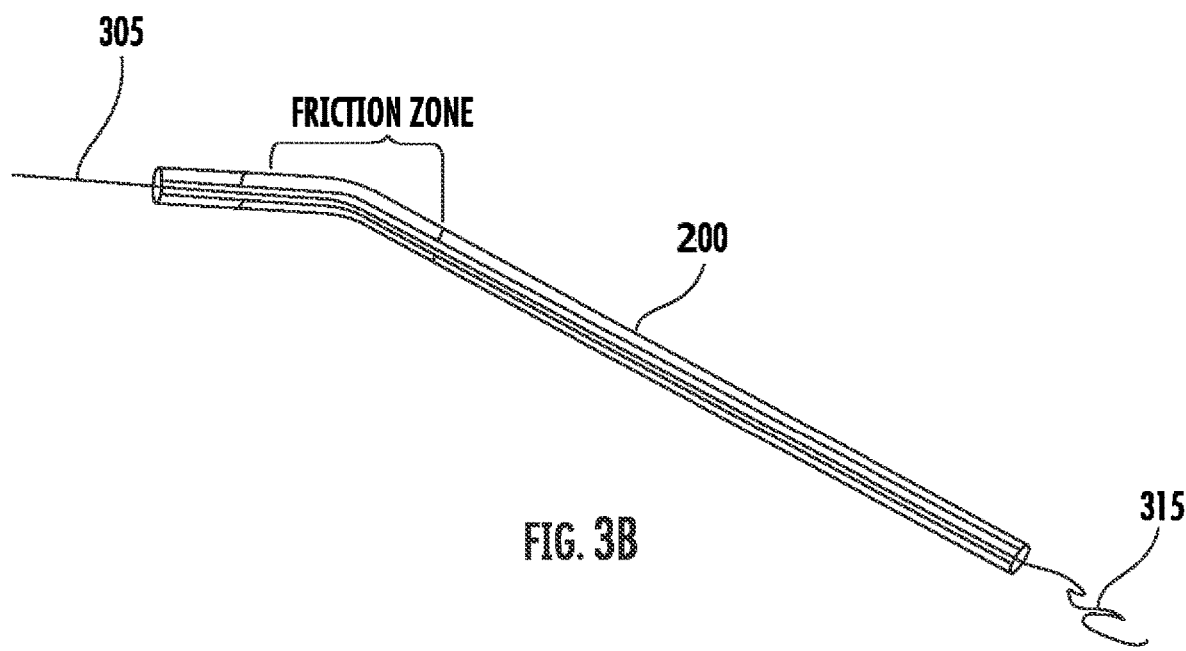
FIG. 3B is a longitudinal cross-sectional view of the present invention intravascular intervention system of FIG. 3A.

By way of illustrative example, experimental testing was performed to measure the frictional force between the introducer sheath 200 and delivery system 305 loaded with an implantable intravascular device 315 that together as a unit are slidable therethrough (as shown in FIGS. 3A & 3B). Testing was performed on an introducer sheath having a heat shrink sleeve made of polyolefin disposed about the outer surface of the introducer sheath positioned approximately 30 mm in a distal direction from the proximal end 206 of the introducer sheath. The heat shrink sleeve used during testing was 2 cm in length in an axial/longitudinal direction having an expanded state of approximately 0.045" and a recovered state of approximately 0.017" (representing the inner diameter of the introducer before and after heating, respectively). With the heat shrink sleeve properly positioned at the desired proximal section along the outer surface of the introducer sheath, a curved mandrel having a diameter of 50.5 mm and an outer diameter of 0.01654" was inserted into the lumen of the introducer sheath until the curvature of the mandrel aligned with the heat shrink sleeve. Using a heat gun thermal heating at a temperature of 325° F. for 30 sec. resulted in curvature or bending of the introducer sheath to match/conform with that of the mandrel simultaneously as the heat shrink sleeve shrunk about the outer surface of the curved proximal section of the introducer sheath. Following cut off of the heat and withdraw of the mandrel from the introducer sheath the heat shrink material of the sleeve cooled and hardened to conform to that of the curved or bent proximal section of the introducer sheath (also matching that of the withdrawn curved mandrel).

Figure 3C:
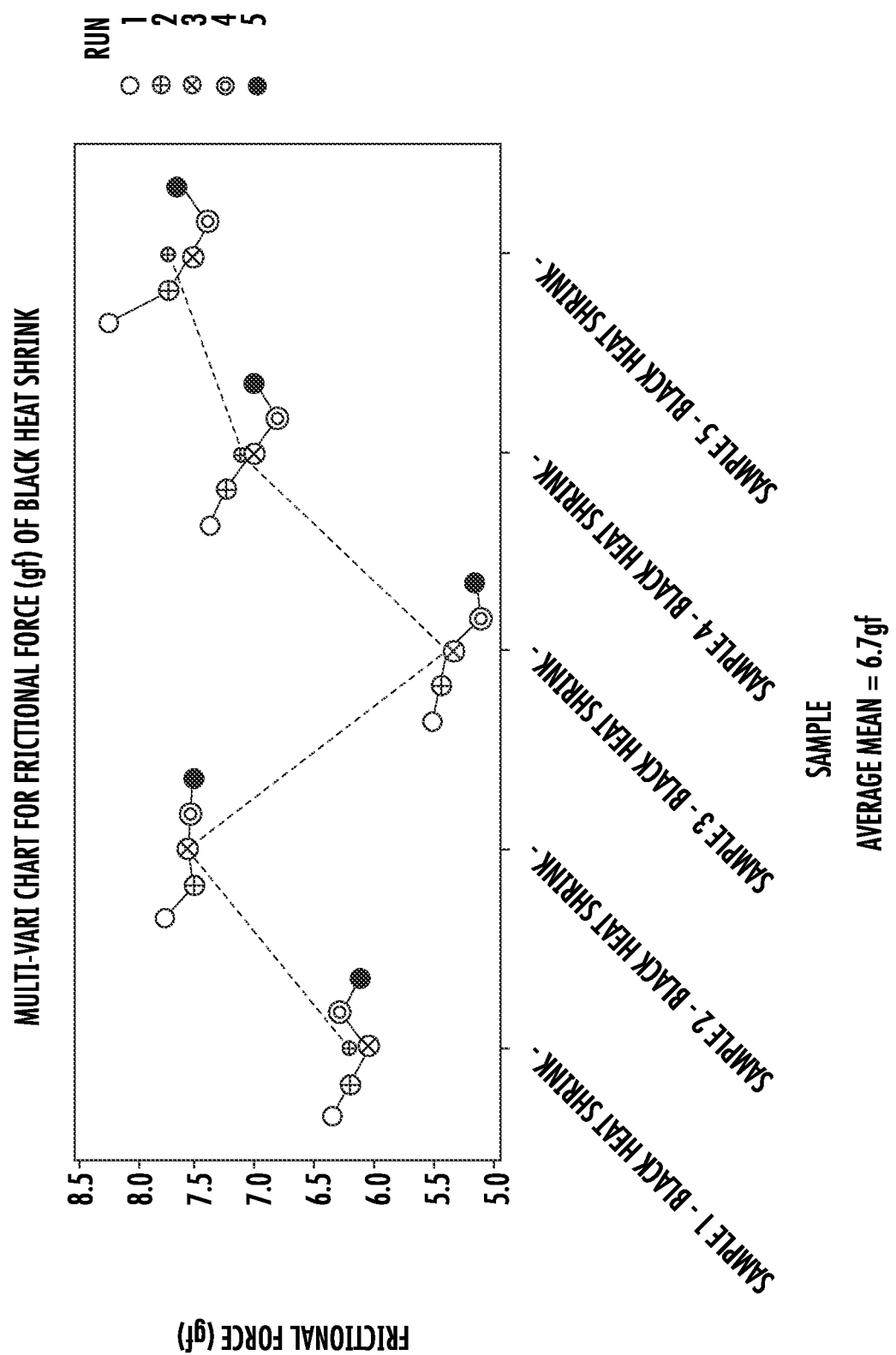
FIG. 3C is a graphical representation of multi-sample testing of the measured frictional force between the delivery system advanced through the exemplary non-straight (curved or bent) intentional friction zone introducer sheath of FIG. 3A.

FIG. 3C shows for five different sample heat shrink sleeves each constructed using the same materials and methods with each sample being tested for 5 different runs, a graphical representation of the measured frictional force (gf) along the intentional friction zone when the delivery system engages with the inner wall of the introducer sheath of FIGS. 3A & 3B. In light of the fact that the parts tested were hand-made, the measured 5 gf-8 gf range of measured frictional force is deemed consistent and effectively equivalent with an average frictional force of 6.7 gf among the samples tested.

Figure 4A:
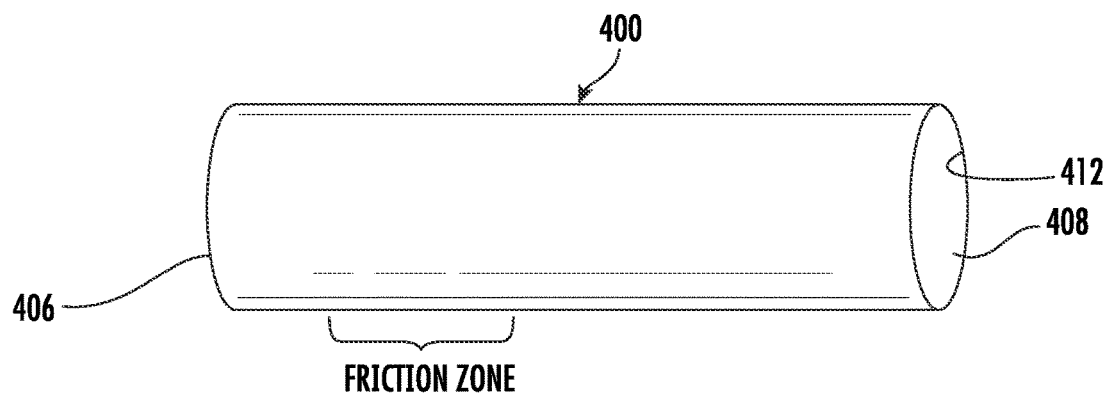
FIG. 4A is a side view of an exemplary alternative embodiment of a present inventive straight (non-bent or non-curved) introducer sheath along a proximal section of which peelable heat shrink tubing is fused to the inner wall reducing the inner diameter forming an intentional friction zone.
Figure 4B:
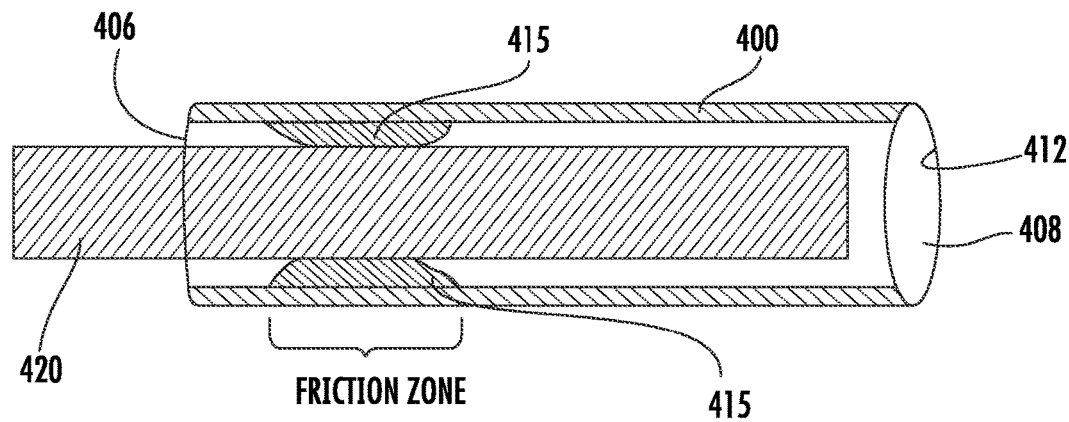
FIG. 4B is a longitudinal cross-sectional view of the present inventive introducer sheath of FIG. 4A with a straight mandrel inserted in the lumen thereof in order to fuse the peelable heat shrink tubing to the inner wall of the introducer sheath.
Figure 4C:
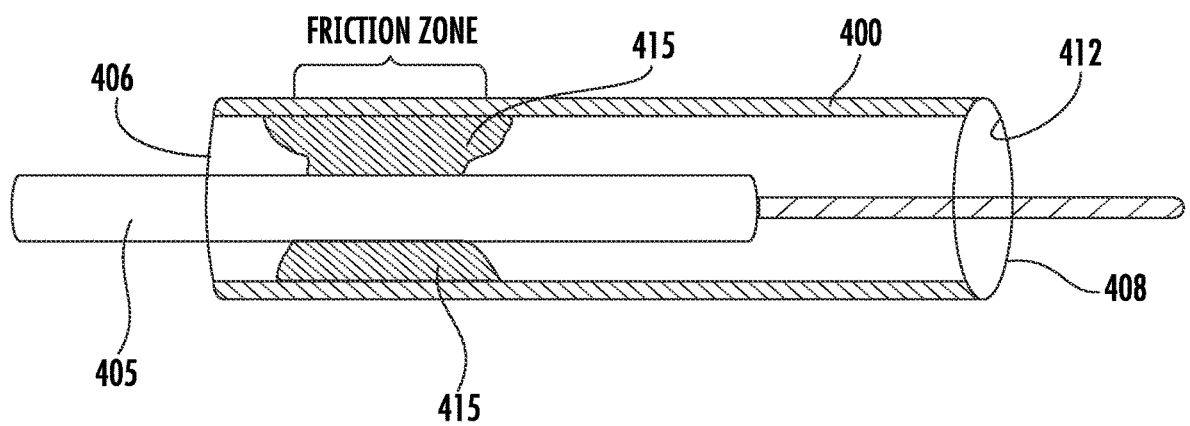
FIG. 4C is an exemplary assembly of the reduced inner diameter friction zone introducer sheath of FIG. 4A together with a delivery system having an implantable intravascular device loaded therein.

In the previous described configuration (FIGS. 3A & 3B) employing a controlled or targeted curve or bend along a proximal section of the present inventive introducer sheath as the intentional friction zone the inner diameter of the introducer sheath is substantially uniform from the proximal to the distal end of the tubing including along the non-straight intentional friction zone. The inner diameter is described as substantially uniform because pressure from the heat shrink sleeve when heated may, but need not necessarily, result in unintended de minimis or negligible collapse (reduction) of the inner diameter of the lumen in the friction zone. In an alternative design shown in FIGS. 4A-4C, the introducer sheath 400 retains its straight (non-bent or non-curved) (parallel to the longitudinal axis) configuration while the friction zone is created along a section thereof by intentionally reducing the inner diameter (e.g., applying to the inner wall a supplemental material). For example, an approximately 5% intentional reduction of inner diameter of the introducer sheath is created along the friction zone. Specifically, a reflowable material 415 (preferably a peelable tubing made of a heat shrink material) is fused to the inner wall along a section of the straight cylindrical tubing 400 between its proximal and distal ends, 406, 408, respectively (FIG. 4A). Referring to FIG. 4B, a straight (non-bent, or non-curved) (i.e., parallel to the longitudinal axis extending therethrough) mandrel 420 is inserted into the lumen 412 of the straight cylindrical tubing 400. Heat is applied at a predetermined temperature and for a specified period of time using a heat gun or other thermal source causing reflow of the peelable heat shrink tubing 415 along the inner wall of the introducer sheath straight cylindrical tubing 400. After removal of the heat and mandrel, the cooled peelable heat shrink tubing 415 shrinks reducing or narrowing the inner diameter of the straight cylindrical tubing 400 creating the intentional friction zone through which the delivery system 405 directly physically contacts or directly engages therewith, as depicted in FIG. 4C. For instance, the resulting introducer may have an inner diameter reduced by approximately 5% (e.g., reduction of approximately 0.0005"). As an illustrative example, for a delivery system having an outer diameter (OD) of 0.0152" and an introducer sheath having an inner diameter (ID) 0.0165", along the friction zone the introducer sheath has an approximate 5% reduction in inner diameter (e.g., an introducer sheath having a 0.0165" inner diameter produces a resulting/reduced inner diameter of approximately 0.0157") producing a friction fit therebetween the two components.

By way of illustrative example, experimental testing was performed to measure the frictional force when the delivery system is advanced through the lumen of the introducer sheath having a configuration in FIG. 4A-4C. Testing was performed on an exemplary introducer sheath having a peelable heat shrink tubing 2 cm in length in an axial/longitudinal direction made of polyolefin having an expanded state of approximately 0.039" and a recovered state of approximately 0.028" (representing the inner diameter of the introducer before and after heating) disposed about the outer surface of the introducer sheath positioned approximately 50 mm in a distal direction from the proximal end of the introducer sheath. With heat shrink sleeve properly positioned at the desired proximal section along the outer surface of the introducer sheath, a straight or linear mandrel having an outer diameter of 0.015" was inserted into the lumen of the introducer sheath. Using a heat gun or other thermal source, the proximal section of the introducer sheath where the peelable heat shrink tubing is applied is heated to a temperature of 350° F. for 30 sec. resulting in reflow of the peelable heat shrink tubing causing a reduction/narrowing in inner diameter of the lumen of the introducer sheath smaller than the outer diameter of the delivery system slidable therethrough thereby imposing the friction force therebetween. The precise parameter ranges were for the specific example with which the tests were run, however, these parameter ranges are non-limiting and may be varied, as desired. For example, the proximal edge of the heat shrink tubing may be positioned to coincide or align with the proximal end of the introducer sheath and extend in a range from approximately 30 mm to approximately 100 mm in a distal direction.

Figure 5:
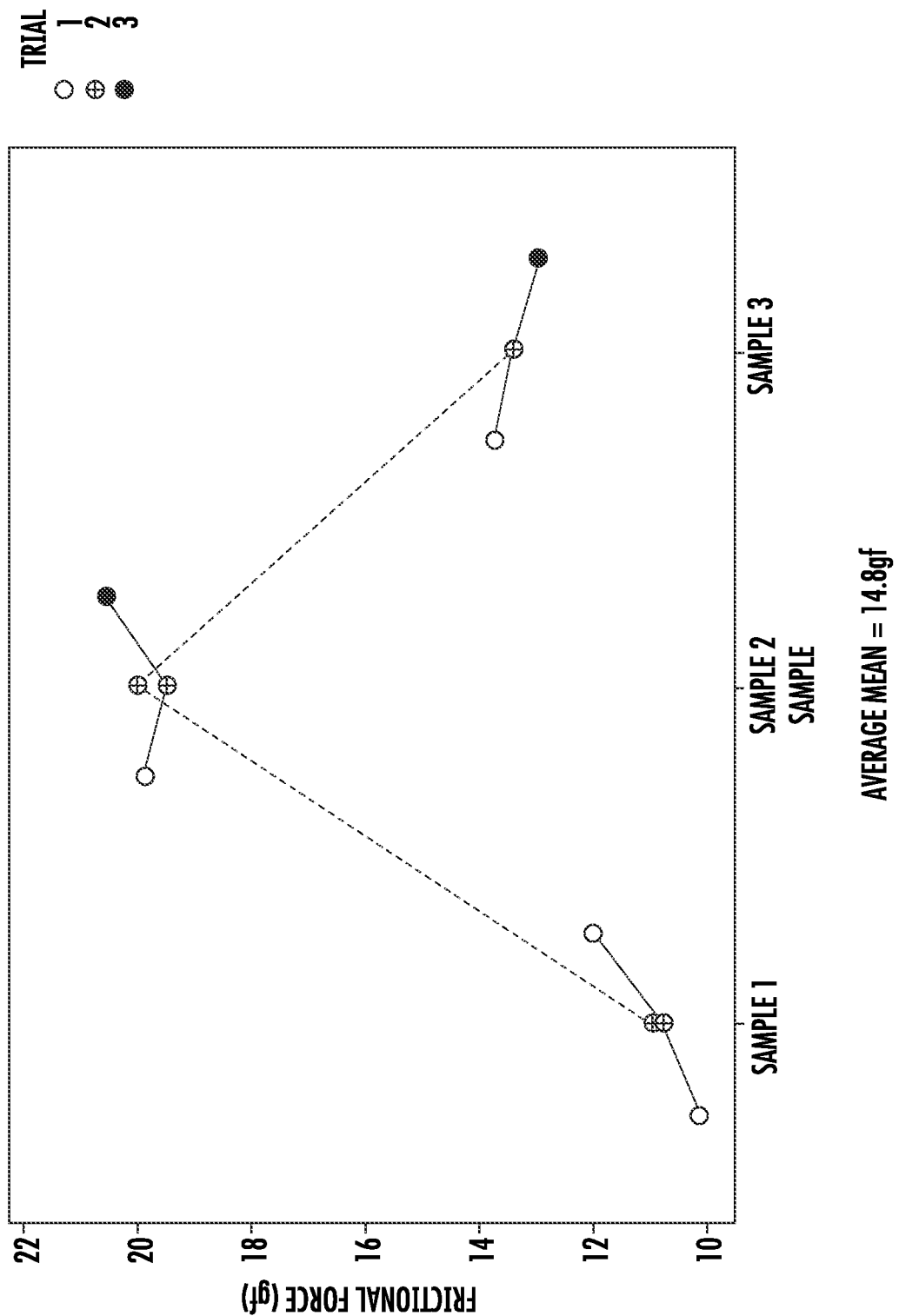
FIG. 5 is an exemplary graphical representation of multi-sample testing of the frictional force measured between the outer surface of the delivery system and the present inventive introducer sheath of FIG. 4A.

FIG. 5 is a graphical representation of the measured frictional force (gf) of three different samples in which peelable heat shrink tubing was applied to a proximal section of the inner wall of the introducer sheath that forms the intentional friction zone where the introducer sheath and delivery system directly physically contact or directly engage one another in the assembly of FIG. 4C. The graph shows each of three samples having three trials/runs, as depicted by the distinct circular symbols provided in the legend located on the right-hand side of the graph. Among the samples tested the average measured frictional force was 14.8 gf. The graphical representation among the multi-samples tested in FIG. 5 illustrates that the consistency and repeatability of achieving a desired targeted or controlled frictional force is less than that when using the shaped (curved or bent) configuration of the introducer sheath (FIGS. 2A-2B), as shown in FIG. 3C.

Figure 6:
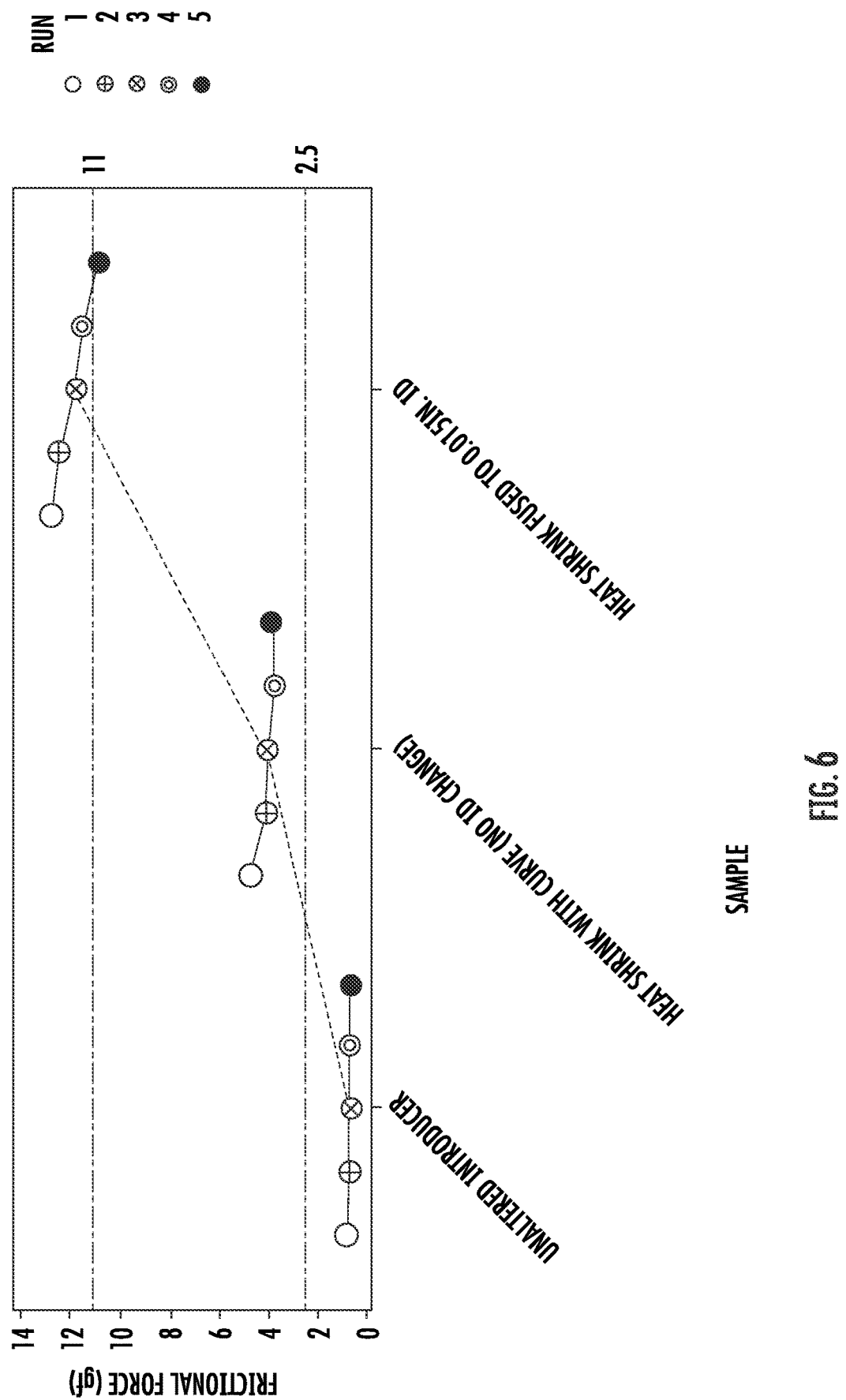
FIG. 6 is a graphical representation comparison of repeatability testing results of the measured frictional force for each of the present inventive introducer sheaths represented in FIGS. 3A & 4C in comparison with that of the conventional straight introducer sheath of FIG. 1 (unaltered—without an intentional friction zone)

FIG. 6 is a graphical representational comparison of detected/measured frictional force among the following three different introducer sheath configurations: (1) first configuration: a conventional ("unaltered") introducer sheath having a straight configuration and a uniform inner diameter therethrough (i.e., absent or free of any intentional friction zone); (2) second configuration: an introducer sheath having an intentional targeted or controlled friction zone comprising a non-straight (bent or curved) (i.e., non-parallel to the longitudinal axis) section with a sleeve of heat shrinkable material disposed about the outer surface thereof, wherein the lumen of the introducer sheath has a substantially uniform inner diameter (i.e., substantially no inner diameter (ID) change); and (3) third configuration: an introducer sheath having a straight configuration producing an intentional targeted or controlled friction zone along a section of the introducer sheath (having a 0.015" inner diameter) in which the inner wall has fused thereto a heat shrink material with a reduced/narrowed inner diameter relative to the inner diameter outside the friction zone. Along the x-axis each introducer sheath configuration is represented, while the measured/detected frictional force is represented along the y-axis. For each of the three introducer sheath configurations frictional force measurements were obtained for five different trials/runs (five data points denoted in FIG. 6 by different symbols (identified in the right-hand-side legend)). The horizontal dashed lines depict a preferred range of frictional force from 2.5 gf (lower line) to 11 gf (upper line). As is evident from the graphical representational comparison, the measured/detected level of frictional force for all five trials/runs taken with the first configuration introducer sheath was less than the preferred minimum of 2.5 gf. Such result for this conventional introducer sheath is expected since intentional or deliberate friction between the components is to be avoided. Among the remaining two introducer sheath configurations of the present invention having an intentional friction zone the best results were achieved with the second configuration. Results of the measured/detected frictional force for the five trial/runs using the third configuration introducer sheath is an improvement over that of the first configuration but not as consistent as when using the second configuration. That is, when testing the frictional force imparted using the third configuration introducer sheath only one of the five trials/runs fell within the preferred range of approximately 2.5 gf to approximately 11 gf, the remaining four runs undesirably imposed a friction force greater than the preferred maximum value of 11 gf. In such cases where the friction force exceeded 11 gf, use of the delivery system to advance the implantable intravascular device (e.g., embolic coil) to the target site in the artery may undesirably require the application of too large an axial force to overcome the friction force. Thus, the third configuration of the introducer sheath in accordance with the present invention although not as consistent and reliable as that of the second configuration of the present inventive introducer sheath is nevertheless more advantageous than a conventional device (e.g., first configuration) free or absent of any intentional friction zone.

Any number of one or more parameters such as, but not limited to, heating parameters (e.g., temperature; duration of exposure to heat; continuous vs. intermittent application of heat); length of tubing in an axial direction; method of heating; and severity of the curve may be selected, as desired, to control the level, amount or degree of friction force imparted on the delivery system when slid through the lumen of the introducer. Regardless of the configuration used to create the friction zone (e.g., non-straight shape vs. reduction in inner diameter), the desired range of imparted frictional force is preferably between approximately 2.5 gram-force (gf)-approximately 11 gram-force (gf). In more broad terms, on the one hand, the desired friction force imposed in the friction zone of the introducer sheath may nevertheless be overcome upon application of a sufficient axial force (pushing) applied to the proximal end of the delivery system with the implantable intravascular device loaded therein that together as a unit are slidable though the lumen of the introducer sheath during delivery to the target site in the artery. While, on the other hand, the imposed friction force is sufficiently strong so that when the implantable intravascular device is precisely located at the target site the position of the delivery system within the introducer sheath is held or maintained (i.e., substantially free from movement, translation or shifting) therein. Moreover, the friction force imposed is also sufficient to prevent the delivery system from falling out from the proximal end of the introducer sheath when a flushing fluid (e.g., saline) is introduced in a retrograde direction.

Figure 7:
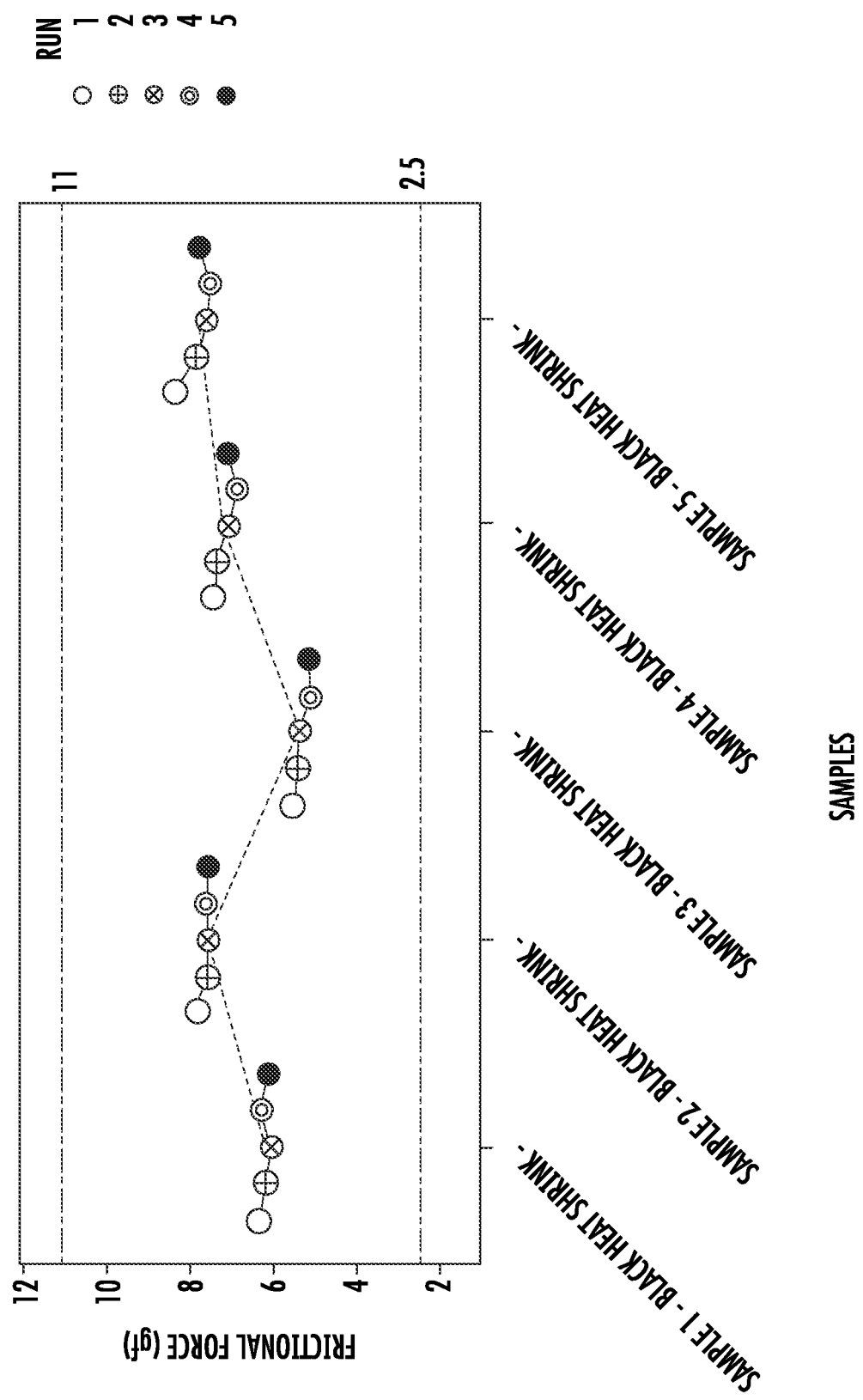
FIG. 7 is a graphical representation of measured frictional force for the present inventive intravascular intervention system in FIG. 3A (curved introducer sheath with a heat shrink sleeve and no variation in inner diameter) for five different samples, each single sample having five different tests/runs (depicted by different symbols identified in the right-hand-side legend)

FIG. 7 is a graphical representation of measured frictional force with the configuration of the present inventive introducer sheath represented in FIG. 3A having a non-straight (curve) configuration and a black heat shrink sleeve (with substantially no variation in inner diameter) for five different samples each sample having five different tests/runs (depicted by different symbols identified in the right-hand-side legend). Among the 25 total runs the extremely high degree of reliability and predictability of imposed frictional force within the preferred range using the second configuration introducer sheath is evident.

Figure 8:
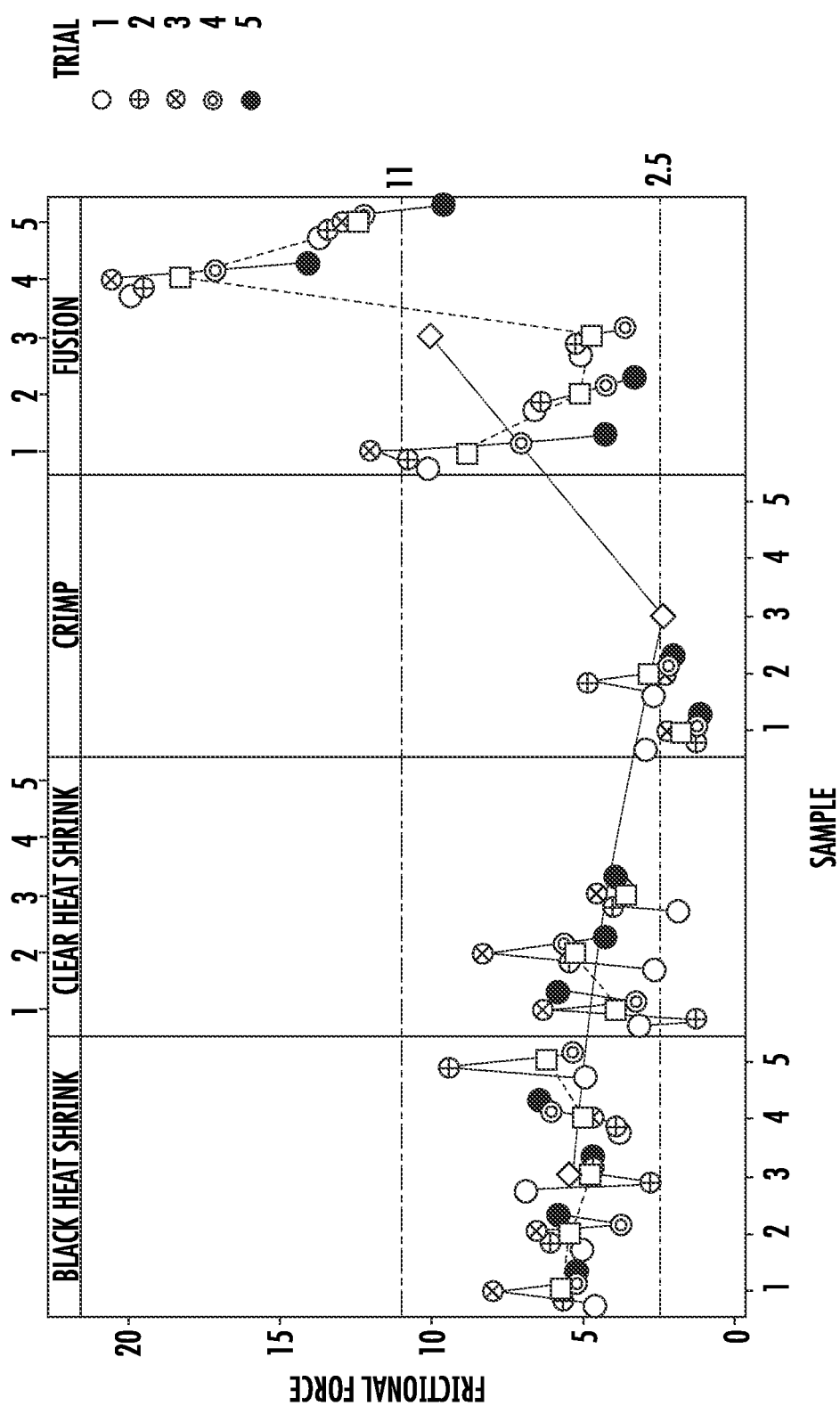
FIG. 8 is a graphical representation comparison of measure frictional force for four different configurations: (i) a non-straight introducer sheath with a curved section intentional friction zone and black heat shrink sleeve (substantially no variation in inner diameter); (ii) a non-straight introducer sheath with a curved section intentional friction zone and clear heat shrink sleeve (substantially no variation in inner diameter); (iii) an introducer sheath with a curved or bent section intentional friction zone but no heat shrink sleeve (substantially no variation in inner diameter); and (iv) a straight introducer sheath with a peelable heat shrink tubing fused to the inner wall thereby reducing/narrowing the inner diameter as the intentional friction zone; each of the four configurations having multiple samples with each of the samples having multiple tests/runs.

FIG. 8 is a graphical representation comparison among the following four different configurations of the present inventive introducer sheath: (i) first configuration—black heat shrink sleeve disposed about a curved section of the introducer sheath having a substantially uniform inner diameter; (ii) second configuration—clear heat shrink sleeve disposed about a curved section of the introducer sheath having a substantially uniform inner diameter; (iii) third configuration—mechanically bent or curved introducer sheath without any heat shrink sleeve; and (iv) fourth configuration—straight introducer sheath (no curved or bent section) with heat shrink material fused along the inner wall thereby reducing or narrowing its inner diameter along a section thereof. Testing was conducted with each configuration—specifically between 2-5 samples were tested for each configuration with each sample having 5 runs/trials (as depicted by the different symbols identified in the right-hand-side legend). The preferred range of imposed frictional force is denoted by the two horizontal dashed lines of 2.5 gf (lower dashed line) and 11.0 gf (upper dashed line). For each of the first and fourth configurations, the testing included five samples of each configuration, with each sample having five runs/trials. Each of the second and third configurations were tested using only three and two samples, respectively, with each sample having five runs/trials.

A comparison between the first and second configurations of the introducer sheath establishes that all 25 runs/trials for all five samples having the first configuration (black heat shrink sleeve) the imposed frictional force reliably and consistently fell within the preferred range, whereas with the second configuration (clear heat shrink sleeve) several of the runs associated with each of the three samples fell outside the preferred range. A greater number of samples and their associated runs/trials fell outside the preferred range of imposed frictional force when using the third configuration relative to that with the second configuration. A still greater number of samples and their associated runs/trials fell outside the preferred range of imposed frictional force with the fourth configuration relative to that of any other configuration. For each of the four configurations, the average imposed frictional force among the associated runs/trials of the different samples is denoted by a single diamond shape data point for that configuration. Once again from this line representing the average imposed frictional force it is evident that the most reliable and consistent imposed frictional force falling within the preferred range is provided by the first configuration.

The present inventive universal introducer sheath has been shown and described with respect to a delivery system loaded with an embolic coil during a coil embolization procedure in the treatment of an intracranial aneurysm. It is contemplated and within the intended scope of the present invention to utilize the present inventive universal introducer sheath for other types of implantable intravascular devices used in other endovascular treatment procedures. The positioning, location or placement of the intentional or deliberate friction zone may be selected, as desired, anywhere along the entire length of the introducer sheath including and between the proximal and distal ends. It is also possible to vary the axial length of the friction zone. Furthermore, more than one friction zone may be provided. In selection of the placement, number and dimensions of the friction zone the parameters may vary to realize a targeted or controlled degree of frictional force imposed on the delivery system being slid therethrough. As previously noted, the imposed frictional force should be able to be overcome by application of an axial force when sliding the delivery system through the introducer sheath to the target site in the vessel, yet sufficient to retain/maintain/hold the delivery system in place when it has reached the target site to ensure deployment of the intravascular device at the intended site in the artery.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. An intravascular intervention system comprising:
an introducer sheath having a proximal end, an opposite distal end and a longitudinal lumen defined therethrough forming an inner wall of the introducer sheath; the introducer sheath having an intentional friction zone along a section of the inner wall of the longitudinal lumen; wherein the intentional frictional zone is a non-straight section of the introducer sheath with a sleeve disposed about an outer surface of the non-straight section of the introducer sheath; the sleeve and the introducer sheath each being made of a heat moldable material matching one another in heat molded shape along the non-straight section; and the sleeve having a proximal edge disposed a predetermined distance in a distal direction relative to the proximal end of the introducer sheath.

2. The intravascular intervention system in accordance with claim 1, further comprising a catheter shaft slidable through the longitudinal lumen of the introducer sheath; wherein the intentional friction zone imposes the intentional frictional force on the outer surface of the catheter shaft in a range of approximately 2.5 gf to approximately 11 gf.

3. The intravascular intervention system in accordance with claim 1, wherein the heat molded shape along the non-straight section of the introducer sheath is curved or bent.

4. The intravascular intervention system in accordance with claim 3, wherein the sleeve maintains shape, configuration and degree of curvature of the curve or the bend of the heat molded shape along the non-straight section of the introducer sheath.

5. The intravascular intervention system in accordance with claim 1, wherein the intentional friction zone is disposed along a proximal section and/or a distal section of the introducer sheath.

6. The intravascular intervention system in accordance with claim 1, wherein an inner diameter of the longitudinal lumen is substantially uniform from the proximal end to the opposite distal end including along the intentional friction zone.

7. The intravascular intervention system in accordance with claim 1, wherein the sleeve is made of a heat shrink material.

8. The intravascular intervention system in accordance with claim 1, wherein in the intentional friction zone a heat shrink material is fused to the inner wall of the introducer sheath reducing an inner diameter of the longitudinal lumen relative to the inner diameter of the longitudinal lumen absent the heat shrink material outside the intentional friction zone.

9. The intravascular intervention system in accordance with claim 1, further comprising:
a catheter shaft having a distal end and an outer surface; the catheter shaft being slidable within the longitudinal lumen of the introducer sheath upon application of sufficient force in a distal direction on the proximal end of the catheter shaft to overcome an intentional friction force established via the intentional friction zone and imposed on the outer surface of the catheter shaft; upon the distal end of the catheter shaft reaching a target position beyond the distal end of the introducer sheath, positioning of the catheter shaft within the longitudinal lumen of the introducer sheath being maintainable via the imposed intentional friction force.

10. The intravascular intervention system in accordance with claim 1, wherein the predetermined distance is in a range of approximately 29 mm to approximately 31 mm.

11. A method of manufacturing an introducer sheath of an intravascular intervention system, the method comprising the steps of:
providing a straight introducer sheath having a proximal end, an opposite distal end, and a longitudinal lumen of uniform inner diameter defined therethrough forming an inner wall of the introducer sheath;
positioning a heat shrink sleeve radially about an outer surface of the introducer sheath;
inserting into the longitudinal lumen of the straight introducer sheath a non-straight mandrel;
heating at a predetermined temperature for a predetermined period of time sufficient to cause the introducer sheath to be molded to include along a section of an inner wall of the longitudinal lumen an intentional friction zone conforming to the non-straight mandrel and the heat shrink sleeve to reflow about the molded intentional friction zone forming an assembled structure; wherein the intentional frictional zone is a non-straight section of the introducer sheath with the heat shrink sleeve disposed about an outer surface of the non-straight section of the introducer sheath; the sleeve and the introducer sheath each being made of a heat moldable material matching one another in heat molded shape along the non-straight section; and the sleeve having a proximal edge disposed a predetermined distance in a distal direction relative to the proximal end of the introducer sheath; and
removing the non-straight mandrel from the formed assembled structure including the molded introducer sheath having the intentional friction zone together with the reflow heat shrink sleeve.

12. The method in accordance with claim 11, wherein the non-straight mandrel has at least one curved section that is aligned with the heat shrink sleeve; and the molded intentional friction zone conforms to the at least one curved section.

13. The method in accordance with claim 11, wherein the molded intentional friction zone is disposed along one of a proximal section and/or a distal section of the introducer sheath.

14. The method in accordance with claim 11, wherein the inner diameter of the longitudinal lumen is uniform from the proximal end to the opposite distal end including along the molded intentional friction zone of the introducer sheath.

15. A method for using an intravascular intervention system comprising the steps of:
providing an introducer sheath having a proximal end, an opposite distal end, a longitudinal lumen with an inner diameter defined therethrough extending therebetween the proximal and distal ends forming an inner wall of the introducer sheath; the introducer sheath having an intentional friction zone along a section of the inner wall of the longitudinal lumen; wherein the intentional frictional zone is a non-straight section of the introducer sheath with a sleeve disposed about an outer surface of the non-straight section of the introducer sheath; the sleeve and the introducer sheath each being made of a heat moldable material matching one another in heat molded shape along the non-straight section; and the sleeve having a proximal edge disposed a predetermined distance in a distal direction relative to the proximal end of the introducer sheath;
introducing a catheter shaft into the longitudinal lumen of the introducer sheath being slidable therein; and
applying sufficient force in a distal direction on a proximal end of the catheter shaft overcome an intentional frictional force established by the intentional friction zone of the introducer sheath and imposed on an outer surface of the catheter shaft during advancement to a target position in the vessel;
upon the distal end of the catheter shaft reaching the target position beyond the distal end of the introducer sheath, the position of the catheter shaft within the longitudinal lumen of the introducer sheath being retained by the imposed intentional frictional force.

16. The method in accordance with claim 15, wherein the intentional frictional force imposed on the outer surface of the catheter shaft in a range of approximately 2.5 gf to approximately 11 gf when slid therethrough.

17. The method in accordance with claim 15, wherein the intentional friction zone is a section of the introducer sheath of reduced inner diameter.

18. The method in accordance with claim 17, wherein the section of the introducer sheath having the reduced inner diameter has a heat shrink material disposed along the inner wall of the introducer sheath.

19. The method in accordance with claim 15, wherein the non-straight section is molded with a curved or bent section.

* * * * *